United States Patent [19]

Kollerup et al.

[11] Patent Number: 4,865,973
[45] Date of Patent: Sep. 12, 1989

[54] PROCESS FOR EXTRACTIVE FERMENTATION

[75] Inventors: Finn Kollerup; Andrew J. Daugulis, both of Kingston, Canada

[73] Assignee: Queen's University at Kingston, Kingston, Canada

[21] Appl. No.: 896,002

[22] Filed: Aug. 13, 1986

Related U.S. Application Data

[63] Continuation-in-part of Ser. No. 775,791, Sep. 13, 1985, abandoned.

[51] Int. Cl.$^4$ .................. C12P 37/00; C12P 19/04; C12P 7/48; C12P 7/06; B01D 11/04; B01D 3/34
[52] U.S. Cl. ........................... 435/43; 435/101; 435/144; 435/161; 435/813; 435/822; 435/911; 435/917; 435/935; 435/942; 435/102; 210/634; 203/60; 203/61; 203/62; 203/63; 203/64; 203/DIG. 13
[58] Field of Search ............ 435/72, 93, 243, 101, 435/144, 150, 151, 160, 161, 162, 813, 43, 822, 911, 917, 935, 942, 102; 210/634; 203/DIG. 13, 54, 55, 60, 61, 62, 63, 64

[56] References Cited

U.S. PATENT DOCUMENTS 4,517,298  5/1985  Tedder ............................. 435/160
4,698,303  10/1987  Bailey et al. ..................... 435/139

OTHER PUBLICATIONS

Ishii et al.; *J. Chem. Eng. of Japan*, 18(2):125–130; (1985).
Taya et al., *J. Ferment. Technol.*, 63(2):181–187; (1985).
Minier et al.; *Biotech. & Bioeng.*; 24:1565–1579; (1982).
Wang et al.; *Biotech. & Bioeng. Symp.*, No. 11:555–565 (1981).

Primary Examiner—Elizabeth C. Weimar
Attorney, Agent, or Firm—Richard J. Hicks

[57] ABSTRACT

A process for producing a variety of chemical products, e.g., ethanol, by fermentation in which the product is removed from the fermentation medium as it is formed by liquid-liquid extraction using an extractant for the product which is immiscible with water. The extractant employed is chosen from the following groups: (A) double bond unsaturated aliphatic alcohols having 12 or more carbon atoms; (B) saturated branched chain aliphatic alcohols having 14 or more carbon atoms or mixtures thereof; (C) double bond unsaturated aliphatic acids having 12 or more carbon atoms; (D) aliphatic and aromatic mono-, di- or tri-esters having 12 or more carbon atoms, other than dibutyl phthalate; (E) aliphatic noncyclic ketones and aliphatic aldehydes having 12 or more carbon atoms; and (F) mixtures of extractants from groups (A) to (E) above or mixtures of at least one of the above extractants and at least one other extractant. These extractants are non-toxic to microorganisms used for fermentation, have little tendency to form emulsions and are otherwise suited for the process. The liquid-liquid extraction may thus be carried out in situ in the fermentor, preferably in a continuous stirred tank fermentor.

12 Claims, 5 Drawing Sheets

PROCESS FOR EXTRACTIVE FERMENTATION

This is a continuation-in-part of U.S. patent application Ser. No. 775,791, filed Sept. 13, 1985, now abandoned.

BACKGROUND OF THE INVENTION

I. Field of the Invention

This invention relates to the production of useful chemical products by fermentation. More particularly, the invention relates to fermentation procedures in which the products may be removed from the fermentation medium by liquid-liquid extraction.

II. Description of the Prior Art

It is well known that a variety of chemical products can be prepared by the culturing or fermentation of microorganisms. For example, a number of antibiotics (such as penicillin), acetone/butanol, citric acid, and, of course, ethanol may be produced in this way. A review of various techniques employed for fermentation using the preparation of ethanol as an example is provided in "Biotechnology Report", Biotechnology and Bioengineering, Vol. XXVI, pp. 1003 to 1025 (1984) by Maiorella et. al., the disclosure of which is incorporated herein by reference.

The most significant disadvantage of fermentation procedures is that the product is normally obtained only in dilute form, i.e. as a dilute solution in the aqueous fermentation medium. This is often because of the phenomenon of "end-product inhibition". That is, the rate of production of the product by the microorganism decreases as the product concentration increases, and the microorganism becomes inactivated by the product when the product reaches a certain critical concentration in the fermentation medium. For this reason ethanol, for example, can be obtained by fermentation at a concentration of no greater than about 11-12% (w/v). It is therefore necessary to provide additional steps for the concentration and purification of the product, and such steps are often difficult and expensive. In the case of ethanol, the fermentation medium is normally subjected to high cost aqueous distillation and (when absolute alcohol is required) further steps have to be taken to free the ethanol from the azeotrope it forms with water. Similar difficulties are encountered for other products.

In order to overcome the above drawback, attempts have been made to remove the product from the fermentation medium as the fermentation proceeds so that the product never reaches a harmful or critical concentration. In this way, the microorganism can function for a prolonged period of time at a high production rate. Moreover, by suitably choosing the method of removal of the product, the difficulty and expense of distilling dilute aqueous solutions may be avoided.

One such attempt utilizes a liquid which is immiscible with the aqueous fermentation medium but which is an extractant for the desired product. The product partitions between the extractant and the fermentation medium when the two are brought into contact, so that the concentration of the product in the aqueous fermentation medium is reduced. In practice, however, a number of difficulties are encountered with this process. For example, common water-immiscible solvents are toxic to most microorganisms and so cannot be used for direct contact with an aqueous fermentation medium containing microorganisms. Secondly, stable emulsions are often formed between the fermentation medium and certain extractants and this gives rise to difficulties of separation, blocking of the equipment etc. It is also difficult to find extractants which have a high partition coefficient for the product and which can later undergo separation from the product by inexpensive techniques.

For example Gyamerah and Glover ("Ethanol by Continuous Fermentation using a Combination of Immobilized Yeast and Solvent Extraction," a paper presented at "Advances in Fermentation '83", Chelsea College, London (U.K.) Sept. 21-23, 1983) used n-dodecanol, tributyl phosphate and n-dodecane as extractants, but found that stable emulsions were formed. They attributed the problem of emulsion formation to the presence of yeast cells in the fermentation medium and so attempted to overcome the problem by immobilizing the yeast cells.

Other extractants which have been suggested are straight chain paraffin hydrocarbons (R. K. Finn "Inhibitory Cell Products: Their Formation and Some New Methods of Removal", J. Ferm. Technol. Vol. 44, p. 305-310, 1966); long chain saturated aliphatic alcohols (Wang, Robinson and Lee, "Enhanced Alcohol Production Through On-Line Extraction", Biotechnology and Bioengineering Symp., No. 11, 555-565, 1981); and various polymer systems (International application published under the Patent Cooperation Treaty WO 82/01563, Mattiasson et. al., May 13, 1982). However, it is believed that no truly satisfactory extractants have been discovered, i.e. extractants which enable the process to be operated continuously on a commercial scale at reasonable cost.

SUMMARY OF THE INVENTION

An object of the invention is to provide a process for the production of products by fermentation coupled with liquid-liquid extraction of the products being formed.

Another object of the invention is to provide a new series of extractants which can be used for liquid-liquid extraction of fermentation products from aqueous fermentation media.

Another object of the invention is to provide a process which allows in situ extraction of the product without the need for immobilization of the microorganism.

Yet another object of the invention is to provide a fermentation process which can be operated continuously for a prolonged period of time.

The invention provides a process for producing a product by extractive fermentation in which a substrate is fermented in an aqueous medium by means of a microorganism and the resulting product is removed from the medium by contacting the medium with an extractant for the product which is substantially immiscible in the aqueous medium. The invention employs as the extractant a liquid from any one of the following groups:

A. Double bond unsaturated aliphatic alcohols having 12 or more carbon atoms;
B. Saturated branched chain aliphatic alcohols having 14 or more carbon atoms or mixtures thereof (e.g. guerbet alcohols);
C. Double bond unsaturated aliphatic acids having 12 or more carbon atoms;
D. Aliphatic and aromatic mono-, di- or tri-esters having 12 or more carbon atoms, other than dibutyl phthalate;
E. Aliphatic noncyclic ketones and aliphatic aldehydes having 12 or more carbon atoms; and F. Mixtures of extractants from groups A to E above or mixtures of at least one of the above extractants and at least one other extractant.

The above compounds are substantially non-toxic to most industrially useful microorganisms under the process conditions, tend not to form stable emulsions, have good partition coefficients for common fermentation products, and can be separated from these compounds relatively inexpensively. Hence they combine all the features necessary to make extractive fermentation a feasible commercial process.

Each of the above groups A to E indicates a minimum number of carbon atoms which the extractants may possess. There is no critical maximum number of carbon atoms for each group except that the extractants should of course be liquid under the extraction conditions and the melting points of compounds tend to decrease as the carbon number increases. Accordingly, the practical upper limit of carbon atoms of each group is preferably the maximum number which corresponds to compounds which are liquid at 40° C. Generally, the use of an extractant having a number of carbon atoms close to the minimum for each group is desirable because the product distribution co-efficient tends to decrease with increasing chain length. However, other considerations may be important in the choice of a particular solvent from each group, such as price and availability, so extractants having higher carbon numbers may be preferred in some cases.

The use of the extractant mixtures of Group F above can be particularly advantageous in various circumstances. For example, when more than one product is formed by the fermentation reaction (e.g. during acetone-butanol fermentation), one or more of the components in the extractant mixture may be selective towards a specific product (e.g. acetone). Moreover, extractant mixtures can be employed to adjust and optimize such physical characteristics as the density, boiling range and viscosity of the liquid extractant.

When an extractant other than one of those listed in Groups A to E is used as a component of a mixture according to Group F, the other extractant should be carefully chosen to ensure that it does not impart harmful or disadvantageous characteristics to the extractant mixture, e.g. toxicity to microorganisms or the tendency to form stable emulsions.

Particularly preferred solvents from the above groups are listed below. Some conventional extractants are also listed for comparison and are identified as Group P.

Group A
(A1) oleyl alcohol (cis-9-octadecen-1-ol)
(A2) phytol (3,7,11,15-tetramethyl-2-hexadecen-1-ol)
(A3) isophytol (3,7,11,15-tetramethyl-1-hexadecen-3-ol)

Group B
(B1) isostearyl alcohol e.g. the commercial product sold under the trademark ADOL 66
(B2) isocetyl alcohol e.g. the commercial product sold under the trademark Eutanol G-16
(B3) octyl dodecanol e.g. the commercial product sold under the trademark Eutanol G Group C
(C1) oleic acid (cis-9-octadecenoic acid)
(C2) linoleic acid (9,11-octadecadienoic acid)
(C3) ricinoleic acid (12-hydroxy-9-octadecenoic acid)

Group D
(D1) dodecyl acetate ($CH_3COO(CH_2)_{11}$)
(D2) butyl dodecanoate ($CH_3(CH_2)_{10}COOC_4H_9$)
(D3) dibutyl sebacate ($C_4H_9OOC(CH_2)_8COOC_4H_9$)
(D4) di(2-ethylhexyl)sebacate ($C_8H_{17}OOC(CH_2)_8COOC_8H_{17}$)
(D5) dibutyl adipate ($C_4H_9OOC(CH_2)_4COOC_4H_9$)
(D6) di(2-ethylhexyl)adipate ($C_8H_{17}OOC(CH_2)_4COOC_8H_{17}$)
(D7) di(2-ethylhexyl)phthalate ($C_8H_{17}OOCC_6H_4COOC_8H_{17}$)
(D8) di(3,5,5-trimethyhexyl) phthalate ($C_8H_{17}OOCC_6H_4COOC_8H_{17}$)
(D9) glycerol tridecanoate ($[CH_3(CH_2)_8COOCH_2]_2CHOCO(CH_2)_8CH_3$)

Group E
(E1) 2-dodecanone ($CH_3CO(CH_2)_9CH_3$)
(E2) dodecanal ($CH_3(CH_2)_{10}CHO$)

Group F
(F1) the commercial product sold under the trademark ADOL 85 NF (69 percent oleyl alcohol)
(F2) the commercial product sold under the trademark ADOL 330 (62 percent oleyl alcohol)
(F3) the commercial product sold under the trademark HD oleyl alcohol (commercial oleyl alcohol)

Group P (prior art extractants)
(P1) 1-dodecanol (lauryl alcohol)
(P2) dibutyl phthalate ($C_6H_4[COOC_4H_9]_2$)
(P3) tributyl phosphate ($[C_4H_9]_3PO_4$)
(P4) PPG 1,000 (polypropylene glycol, having an average molecular weight of 1,000)

The Table below lists the pertinent physical data for each of the above compounds, including the conventional compounds of Group P for comparison. In the Table, the compounds are identified by the letter and number in brackets which precedes each of the compounds in the above list.

The Table gives the following information for each compound: (a1) distribution coefficient in fermentation broth, (a2) distribution coefficient in distilled water; (b) emulsion tendency; (c1) normal boiling point, (c2) melting point, (c3) liquid density, (c4) latent heat of vaporization, (c5) molecular weigt, (c6) lethal dose fifty; biocompatibility data in the form of (d1) percent survival, (d2) percent metabolic activity and (d3) biocompatibility rating; mutual solubilities (e1) solvent in water, and (e2) water in solvent.

TABLE
PHYSICAL DATA OF THE EXTRACTANTS

| EXTRACTANT DATA | A1 | A2 | A3 | B1 | B2 | B3 | C1 | C2 | C3 |
|---|---|---|---|---|---|---|---|---|---|
| (a) DEtOH, g/g | | | | | | | | | |
| 1: in ferm. broth | .289 | .306 | .157 | .192 | .152 | .127 | .171 | .209 | NA |
| 2: in dist. water | .166 | .248 | .219 | .251 | .223 | .181 | NA | .107 | NA |
| (b) emulsion tendency | 1 | 0 | 1 | 0 | 0 | 1 | 1 | 0 | 1 |
| (c) 1: NBP, deg. C. | 360 | 355 | 375 | 360 | 300 | 350 | 370 | 395 | 410 |
| 2: MP, deg. C. | +16 | <20 | <20 | +8 | −13 | <20 | +5 | −12 | +6 |
| 3: DENS, g/ml | .849 | .850 | .843 | .861 | .842 | .850 | .895 | .902 | .940 |
| 4: Hvap, cal/g | 49 | 44 | 46 | 45 | 50 | 44 | 72 | 50 | 48 |
| 5: MOL. WT. cal/g | 269 | 297 | 297 | 295 | 242 | 299 | 282 | 281 | 298 |

TABLE-continued

PHYSICAL DATA OF THE EXTRACTANTS

| | | | | | | | | | |
|---|---|---|---|---|---|---|---|---|---|
| 6: LD50, g/kg | 26 | NA | NA | 20 | 6.4 | NA | NA | NA | NA |
| (d) biocompatibility | | | | | | | | | |
| 1: % survival | 96 | 100 | 101 | 104 | 103 | 115 | 100 | 90 | 10 |
| 2: % activity | 98 | 105 | 95 | 100 | 97 | 100 | 100 | 102 | 10 |
| 3: rating | B | B | B | B | B | B | B | B | I |
| (e) mutual solubility | | | | | | | | | |
| pct 1: solv. in water | 13.5 | 12.1 | 12.7 | 11.9 | 12.6 | 10.8 | 2.23 | 3.25 | 32.2 |
| ppb 2: water in solv. | 11.3 | 1.07 | 1.85 | 2.73 | 8.36 | 0.29 | 11.6 | 41.2 | 385 |
| EXTRACTANT DATA | A1 | A2 | A3 | B1 | B2 | B3 | C1 | C2 | C3 |

| | EXTRACTANT | | | | | | | | |
|---|---|---|---|---|---|---|---|---|---|
| EXTRACTANT DATA | D1 | D2 | D3 | D4 | D5 | D6 | D7 | D8 | D9 |
| (a) DEtOH, g/g | | | | | | | | | |
| 1: in ferm. broth | .150 | .165 | .116 | .221 | .129 | .093 | .037 | .055 | .108 |
| 2: in dist. water | .044 | .090 | .078 | .058 | .090 | .080 | .093 | .064 | .085 |
| (b) emulsion tendency | 1 | 0 | 1 | 0 | 0 | 1 | 0 | 1 | 1 |
| (c) 1: NBP, dC | 280 | 440 | 344 | 470 | 300 | 420 | 384 | 440 | NA |
| 2: MP, dC | <0 | <0 | <0 | −48 | −38 | −70 | −46 | −30 | +24 |
| 3: r, g/ml | .865 | .860 | 1.12 | .912 | .962 | .922 | .981 | .971 | 1.00 |
| 4: dHvap, cal/g | 51 | 58 | 41 | 37 | 47 | 39 | 35 | 36 | NA |
| 5: MOL. WT. | 229 | 256 | 315 | 427 | 258 | 371 | 391 | 419 | 555 |
| 6: LD50, g/kg | NA | NA | 16 | 1.3 | 13 | 9.1 | 6.5 | NA | NA |
| (d) biocompatibility | | | | | | | | | |
| 1: % survival | 62 | 100 | 100 | 100 | 6 | 100 | 100 | 100 | 100 |
| 2: % activity | 105 | 99 | 103 | 96 | 3 | 101 | 101 | 98 | 103 |
| 3: rating | B | B | B | B | I | B | B | B | B |
| (e) mutual solubility | | | | | | | | | |
| pct 1: solv. in water | 5.06 | 3.73 | 8.42 | 7.20 | 9.51 | 7.71 | 4.82 | 4.87 | NA |
| ppb 2: water in solv. | 35.8 | 10.1 | 0.97 | 0.00 | 86.9 | 0.01 | 0.00 | 0.00 | NA |
| EXTRACTANT DATA | D1 | D2 | D3 | D4 | D5 | D6 | D7 | D8 | D9 |

| | EXTRACTANT | | | | | | | | |
|---|---|---|---|---|---|---|---|---|---|
| EXTRACTANT DATA | E1 | E2 | F1 | F2 | F3 | P1 | P2 | P3 | P4 |
| (a) DEtOH, g/g | | | | | | | | | |
| 1: in ferm. broth | .363 | .514 | .235 | .253 | .208 | .590 | .651 | .886 | .510 |
| 2: in dist. water | .114 | .277 | .278 | .265 | .268 | .477 | .112 | .696 | .401 |
| (b) emulsion tendency | 1 | 1 | 0 | 0 | 0 | 2 | 2 | 1 | 1 |
| (c) 1: NBP, dC | 246 | 260 | 330 | 340 | 330 | 256 | 340 | 289 | NA |
| 2: MP, dC | +21 | +12 | +10 | +22 | +10 | +23 | −40 | <0 | <0 |
| 3: DENS, g/ml | .820 | .835 | .840 | 845 | .860 | .831 | 1.05 | .972 | 1.01 |
| 4: Hvap, cal/g | 77 | 74 | 47 | 49 | 47 | 82 | 64 | 44 | NA |
| 5: MOL. WT. | 184 | 184 | 267 | 261 | 269 | 186 | 278 | 266 | 1000 |
| 6: LD50, g/kg | NA | 2.3 | 26 | 26 | 26 | 13 | 12 | 3.0 | 2.2 |
| (d) biocompatibility | | | | | | | | | |
| 1: % survival | 5 | 10 | 100 | 94 | 95 | 25 | 75 | 0 | 85 |
| 2: % activity | 17 | 15 | 103 | 98 | 100 | 3 | 96 | 2 | 78 |
| 3: rating | I | I | B | B | B | I | B | T | I |
| (e) mutual solubility | | | | | | | | | |
| pct 1: solv. in water | 2.44 | 1.02 | 13.5 | 13.5 | 13.5 | 17.7 | 5.33 | NA | NA |
| ppb 2: water in solv. | 2802 | 713 | 11.3 | 11.3 | 11.3 | 2214 | 2.62 | NA | NA |
| EXTRACTANT DATA | E1 | E2 | F1 | F2 | F3 | P1 | P2 | P3 | P4 |

NOTES RELATING TO THE TABLE
1. (a) Distribution coefficients were calculated on a mass basis, i.e. as ([EtOH]s/[EtOH]a)/DENS(s), where DENS(s) is the density of the solvent, and a density of unity for the aqueous phase is employed. The Distribution coefficient in the fermentation broth was measured as follows: A shake flask containing 50 ml of a 15% glucose medium was inoculated with yeast cells and allowed to grow for 8 hours. At this time, 10 ml of solvent was added to the growing culture. After 24 hours, when virtually all glucose was converted to ethanol, the ethanol concentration in the aqueous and in the solvent phase was measured. The distribution coefficient in distilled water was measured by equilibrating 5 grams of solvent with 5 ml of a 5% (w/v) ethanol solution in distilled water. It is to be noted that in most cases the distribution coefficient observed in the fermentation broth was higher than that in distilled water. This is attributed to a "salt effect" due to the presence of residual glucose, yeast cells etc. in the fermentation broth. Although these distribution coefficients are for ethanol only, it is safe to say that the corresponding distribution coefficients for acetone and butanol will be an order of magnitude higher.
2. (b) The emulsion tendency was rated according to the following scale: 0 - no emulsion tendency, 1 - some emulsion tendency, and 2 - heavy emulsion tendency.
3. (c) Physical Solvent Data. (1) NBP (Normal boiling

TABLE-continued
PHYSICAL DATA OF THE EXTRACTANTS point) was taken as direct experimental data or extrapolated from boiling point data at reduced pressure. (2) MP (melting point) was taken as direct experimental data, when available. (3) DENS (density) - direct experimental data. (4) Hvap (latent heat of vaporization) was taken as direct experimental data or was calculated using Trouton's Rule (Hvap = 21*NBP). (5) MOL. WT. - experimental data. (6) LD50 (oral lethal dose fifty for rats) - experimental data.

4. (d) Biocompatibility Indicators. (1) % survival is the percentage of surviving yeast cells (also known as the cell viability) after exposure for 16 hours to solvent under the conditions outlined in note 1. The cell viability was measured either by dilution plating or by using the methylene blue staining technique [Lee et al., Biotechnol. Bioeng. Symp., 11 (3rd. Symp. Biotechnol. Energy Prod. Conserv.), 641–649, 1981]. (2) % activity was measured as the average of the percentage glucose consumed and ethanol formed, relative to a control culture. (3) The biocompatibility of solvents was rated as either B: biocompatible, I: Inhibitory, or T: toxic. The specific criteria applied in order to distinguish between these three solvent groups were as follows: If no surviving cells appeared in a plate count after solvent exposure, it was rated as toxic, regardless of what other indicators showed. Among the solvents that allowed cells to survive in a plate count, the ones exhibiting ≦90 percent metabolic activity were rated as inhibitory solvents.
The remaining solvents, exhibiting more than 90 percent metabolic activity after solvent exposure, were rated as biocompatible.
It is to be noted that this toxicity information strictly speaking is for yeast cells only. There is good reason to believe, however, that a solvent that is non-toxic to yeast cells, will be non-toxic towards other microorganisms as well.

5. (e) Mutual Solubilities were calculated from UNIFAC [Magnussen et al., Ind. Eng. Chem. Process Des. Dev., 20(2), 331-339, 1981]. (1) The solubility of solvent in water was expressed as mole percent (pct), while (2) the solubility of water in solvent was expressed in mole parts per billion (ppb).

In particular, the Table above shows that the extractants of the invention have no, or only slight, tendency to form emulsions, acceptable biocompatibility, good distribution co-efficients for the product and low water solubility. Hence, they are ideal extractants for use in the present invention.

Examples of the fermentation processes to which the present invention can be applied include the production of ethanol by the fermentation of the yeast *Saccharomyces cerevisiae* (and the bacterium *Zymomonas mobilis*), the production of acetone/butanol by the fermentation of *Clostridium acetobutylicum*, the production of penicillin by the fermentation of *Penicillium chrysogenum*, the production of citric acid by the fermentation of *Aspergillus niger*, and the production of polysaccharides by the fermentation of *Pullularia pullulans*.

It is a particular advantage of the invention that the solvents listed above can be used for in situ extraction of the product. That is, the solvents may be introduced directly into the fermentor where they remove the product from the fermentation medium as the product is being formed. In situ extraction offers the following advantages, namely (i) decreased fermentor costs due to smaller equipment size (capital cost advantage), (ii) decreased product recovery costs due to larger product concentrations (operating cost advantage), and (iii) decreased medium pre-treatment and waste treatment cost due to smaller aqueous flows (operating cost advantage).

Since the extractants have little tendency to form stable emulsions with the fermentation medium in the presence of microorganisms, there is no need to immobilize the microorganism or to separate the microorganism from the fermentation medium before the extraction takes place.

Moreover, since the extractants separate fairly easily from the aqueous fermentation medium, they can easily be removed from the fermentor and replenished, so that the extraction process may be carried out continuously. In a particularly preferred form of the invention, the extractant/product solution removed from the fermentor can be treated to separate the product from the extractant and the extractant can then be recycled to the fermentor for the extraction of further product.

The easy separation of the fermentation medium and extractant also permits the fermentation medium to be withdrawn from the fermentor and fresh substrate solution to be added, if this is desired.

The fermentation process may accordingly be made entirely continuous in that the extractant may be recycled between the fermentor and the separation apparatus and the fermentation medium may be continuously refreshed. Since the end product is not allowed to reach the critical toxic concentration, the fermentation procedure can be carried out indefinitely, or at least for a considerable period of time.

The process is advantageously carried out in a continuous stirred tank fermentor in which the microorganism cells are freely suspended. This allows a high yield to be obtained while utilizing well-proven fermentation technology. In such an apparatus, for steady state operation, the input rate of fresh substrate solution (known as the dilution rate, i.e. the input flow rate divided by the volume of the fermentor) should be such that the rate of cell removal in the outflowing medium is equal to the rate of cell production in the fermentor. In this way the microorganism cell population remains virtually unchanged.

The fact that the present invention permits the use of freely suspended cells in the fermentor is advantageous because free cells may be more productive then immobilized cells since free cells do no encounter the mass transfer resistance often associated with immobilization matrices, and the use of immobilized cells tends to make the process expensive. Moreover, since the extractants are non-toxic and do not form stable emulsions in the presence of the microorganisms, steps do not have to be provided to ensure that cells are removed from the fermentation medium before the liquid-liquid extraction takes place The normal conditions under which the fermentation/extraction procedure takes place are as follows (a) 20°-80° C., (b) vacuum to slightly above atmospheric pressure (0.05-5 atm), (c) pH 3.0-8.0, (d) agitation 0-1000 rpm, (e) aeration 0-5 vvm (liters air/liters fermentation broth-minute), (f) feed concentration 20-800 g/L glucos equivalents, (g) solvent dilution rate 0.1-25 $h^{-1}$. they should not be considered limitative of the present invention.

While continuous fermentation employing a continuous stirred tank fermentor as indicated above is much preferred, the solvents disclosed herein may also be used with batchwise fermentation, or fed-batch fermentation or immobilized cell fermentation if this is desired.

Furthermore, downstream (rather than in situ) extraction may be carried out, if desired. In such a process, the liquid-liquid extraction of the product is carried out on fermentation medium removed from the fermentor. After separation of the aqueous medium from the extractant/product solution, the medium may be recycled to the fermentor, discarded or treated for the removal of any remaining product.

During the extraction step, the extractant is preferably brought into intimate contact with the aqueous medium in order to promote rapid and complete partition of the product. For example, in the case of in situ extraction, the extractant may be introduced in small streams at the bottom of the fermentor and allowed to rise to the surface to form a continuous surface layer.

After separation of the extractant/product solution from the fermentation medium, the product can be removed from the extractant by any suitable means and, as mentioned above, the extractant may then be recovered and reused for further product extraction. For example, the extractant/ product solution may be distilled in order to separate the product from the extractant. Distillation of the extractant solution does not usually require as much energy input as distillation of the fermentation medium itself because the organic extractants have smaller latent heats of vaporization and heat capacities than water, and because the boiling points of the solvents are much higher than that for water, resulting in fewer equilibrium distillation stages. Furthermore, an extractant can easily be chosen which does not form an azeotrope with the product or otherwise affect the product, so that a product of greater purity can be obtained than is often the case with direct distillation of the fermentation medium.

As an alternative to distillation, the product may be separated from the extractant by stripping with air or $CO_2$, followed by product condensation, or by any other suitable method.

Preferred apparatus for carrying out the invention is described below with reference to the accompanying drawings, in which.

The preferred embodiment described below involves the preparation of ethanol by fermentation of a substrate (such as glucose) in the presence of yeast.

Figure 1:
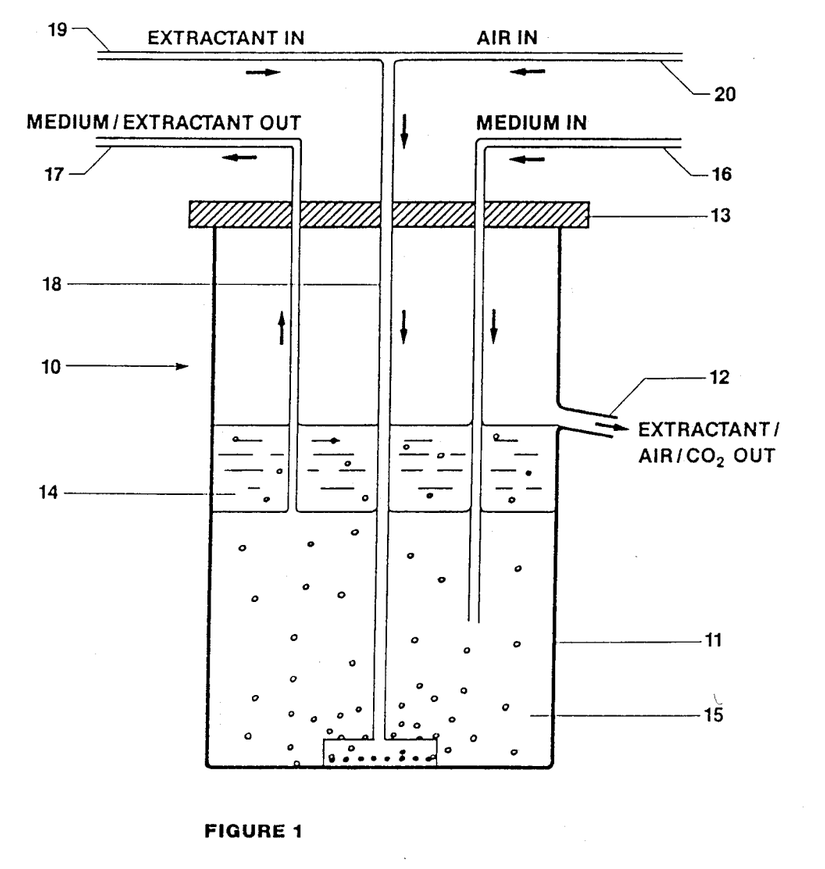
FIG. 1 is a cross-sectional view of a continuous stirred tank fermentor being operated according to a preferred form of the invention.

FIG. 1 shows an example of a continuous stirred tank fermentor 10 suitable for use in the present invention. The fermentor comprises a container 11 having an overflow outlet 12 and lid 13. During use, a layer 14 of extractant overlies an aqueous fermentation medium 15 containing a yeast capable of converting a substrate such as glucose into ethanol. The container 11 may be provided with a mechanical stirrer (not shown), although such a stirrer is not really necessary as will be apparent from the description below.

Fresh medium containing the substrate is introduced into the fermentor on a continuous basis via a pipe 16. The medium, and possibly entrained extractant, is withdrawn from the fermentor on a continuous basis via pipe 17. Since the rates of introduction and removal of the medium ar the same, the surface level of the medium in the fermentor remains essentially unchanged.

Extractant and air (the input of air may not be required for anaerobic fermentations such as those producing ethanol, acetone and butanol) are introduced into the fermentor via a pipe 18 from separate feed pipes 19 and 20, respectively. A dispersion head 21 is located at the bottom of the fermentor and is connected to the extractant/air pipe 18. The dispersion head is provided with a larger number of small holes so that the extractant and air are separated into small streams as they enter the fermentation medium. Since the extractant and air are less dense than the aqueous fermentation medium, both rise to the surface and, as they do so, come into intimate contact with the fermentation medium. The rising air bubbles have the effect of stirring the medium. The extractant removes a portion of the ethanol product from the aqueous fermentation medium as the product is being formed so that the concentration in the fermentation medium itself rarely exceeds 2 to 3% (w/v). In this way, the concentration of ethanol in the aqueous fermentation medium never reaches the 11-12% (w/v) level at which end product inhibition causes the reaction to cease. Carbon dioxide generated during the fermentation also helps to stir the fermentation medium as the gas bubbles rise to the surface.

Since the extractant has little tendency to form an emulsion with the fermentation medium, the layer 14 is substantially free of aqueous medium and can be decanted through the outlet 12. Air and carbon dioxide also leave the fermentor through this outlet. The extractant, which contains the extracted ethanol, then undergoes treatment so that the extractant and ethanol may be removed, as will be explained below.

Yeast cells are removed from the fermentor with the aqueous medium, but the rate of removal may be made such that it is essentially the same as the increase in the yeast cell population as the fermentation proceeds. If desired, however, the yeast cells in the medium removed from the fermentor may be recycled to the fermentor.

Since the fermentor 10 is continuously supplied with substrate and oxygen and since the product is continuously removed to avoid end product inhibition or a reduction of the production rate, the fermentation may proceed indefinitely.

Figure 2:
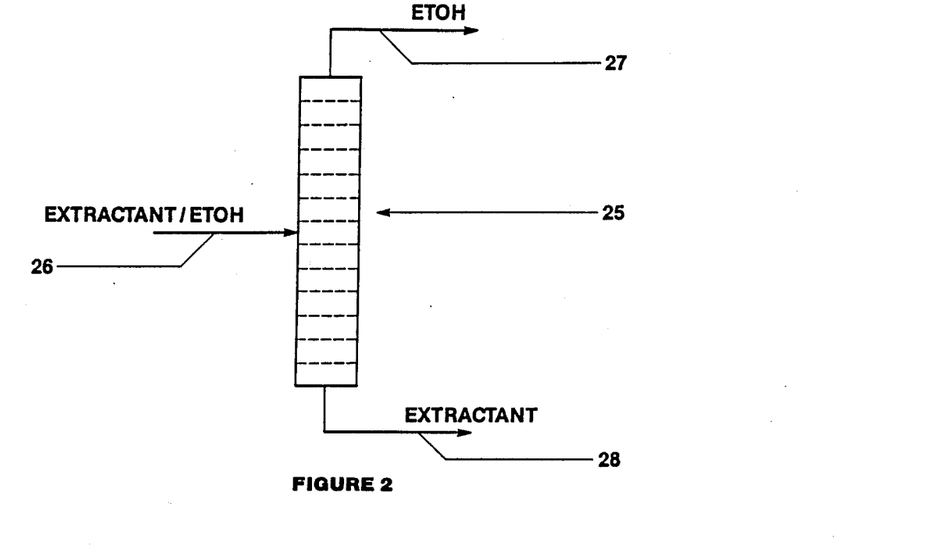
FIG. 2 is a representation of a distillation apparatus for separating the extractant and product.
Figure 3:
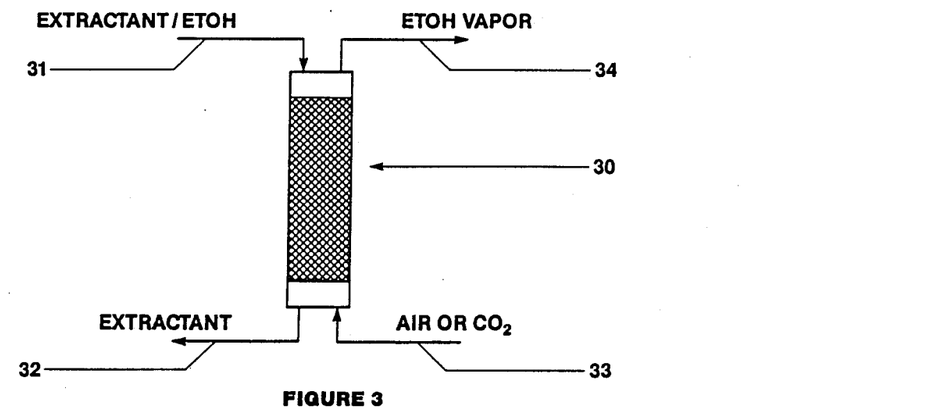
FIG. 3 is a representation of an extractant stripping apparatus which can be used as an alternative to the distillation apparatus of FIG. 3.

FIGS. 2 and 3 are representations of apparatus that may be used to separate the ethanol from the extractant. FIG. 2 shows a distillation apparatus 25 having an extractant solution inlet 26, an upper outlet 27 for the ethanol and a lower outlet 28 for the extractant. The apparatus itself is conventional, so further details need not be provided.

FIG. 3 shows an apparatus 30 for stripping the ethanol product from the extractant. The extractant/ethanol solution enters at inlet 31 and flows downwardly through the apparatus to an outlet 32. Air or carbon dioxide is introduced into the apparatus through an inlet 33 at the bottom of the apparatus and rises in intimate contact with the descending solution to an outlet 34 at the top of the apparatus. The air or $CO_2$ removes the ethanol in the form of vapour from the extractant solution.

Figure 4:
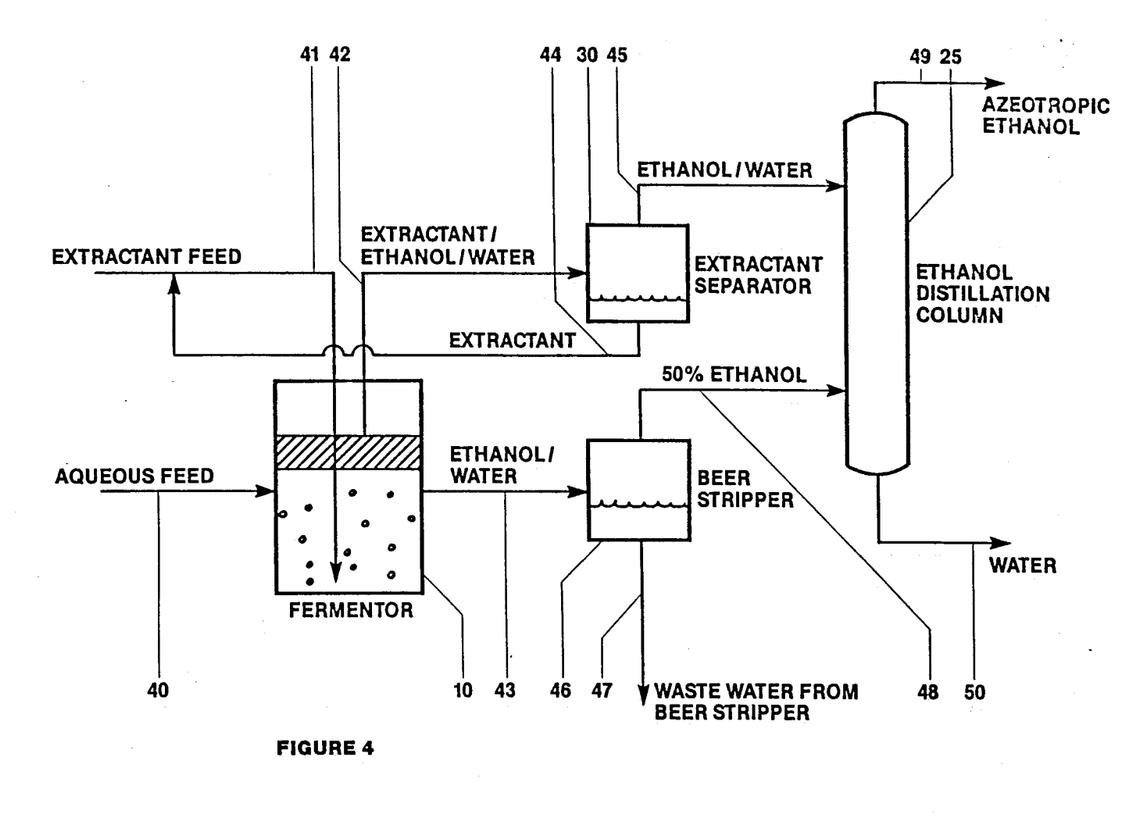
FIG. 4 is a schematic diagram representing an integrated apparatus for continus fermentation, product removal and product isolation.

FIG. 4 shows an integrated apparatus for the continuous production of ethanol by fermentation and liquid-liquid extraction. Where appropriate, the parts of the apparatus illustrated in the previous figures are identified by the same reference numerals.

Fresh medium containing the substrate is introduced into fermentor 10 via aqueous feed line 40. Extractant is introduced into the bottom of the fermentor via extractant feed line 41 and the extractant/ethanol/water mixture is withdrawn via feed line 42. The medium is continuously withdrawn from the fermentor 10 via outlet 43. The extractant/ethanol/water mixture from line 42 is fed to an extractant separator 30. The separated extractant is recycled to extractant feed line 41 via line 44, and the separated ethanol/water mixture is fed to a distillation column via line 45.

The medium extracted from the fermentor 10, which is mainly a mixture of ethanol and water, is fed to a beer stripper 46 which is similar to extractant separator 30. The mixture is separated into a 50% ethanol water solution and a waste water component. The waste water component is discharged through pipe 47 and the 50% ethanol solution is fed to the distillation column 25 via pipe 48.

The ethanol distillation column separates the incoming feeds into azeotropic ethanol, which exits through pipe 49, and water, which exits via pipe 50.

Figure 5:
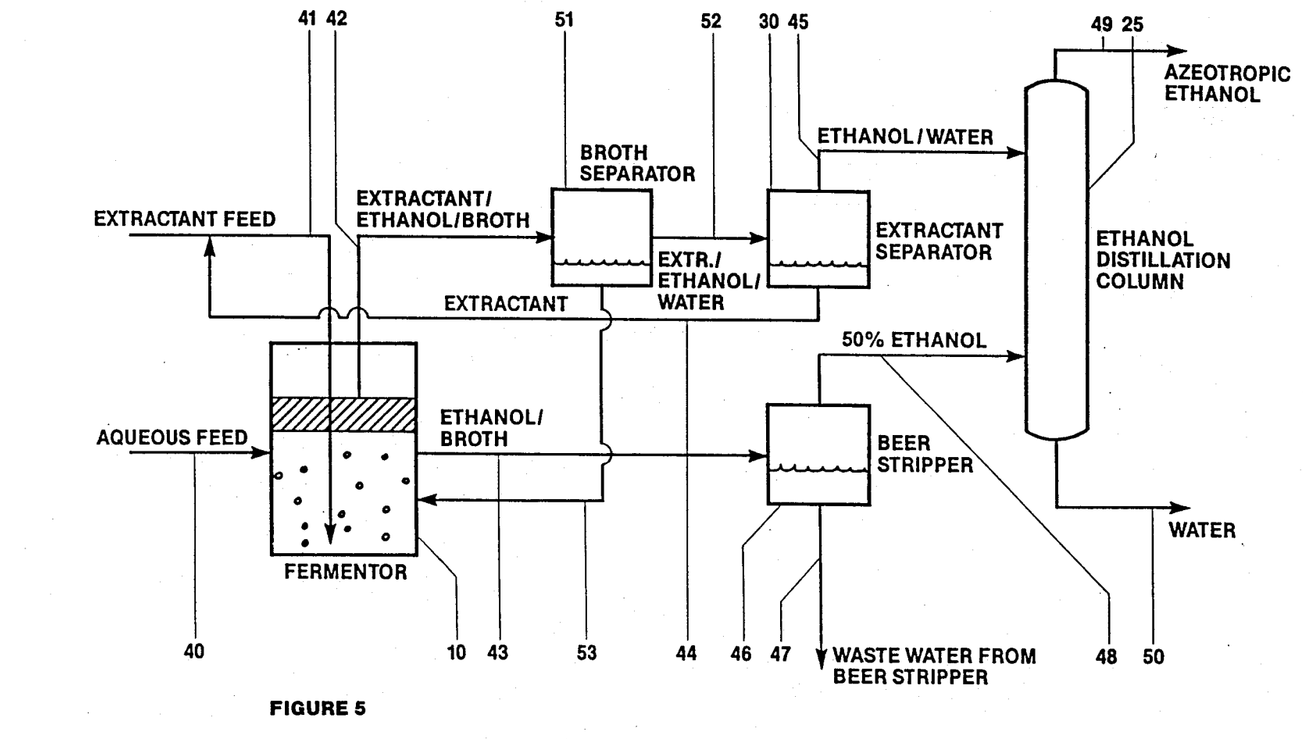
FIG. 5 is a schematic diagram illustrating a preferred, alternative embodiment of the apparatus illustrated in FIG. 4.

During the complete conversion of concentrated substrate feeds (>300 g/L) some association between the extractant and the fermentation broth is unavoidable because the broth becomes entrained into the extractant due to the vigorous evolution of carbon dioxide. This phenomenon may lead to a significant loss of fermentation broth in the extractant stream 42 leaving the fermentor, because the initial water concentration in the aqueous feed 40 is relatively low when concentrated substrate feeds are employed. Thus, it is desirable to control the amount of water in the effluent extractant stream 42. FIG. 5 shows a preferred embodiment of the invention for the production of ethanol by extractive fermentation using concentrated substrate feeds, in which the effluent extractant stream 42 enters a broth separator 51, and is separated into a broth stream 53 (consisting largely of microbial cells in water), which is returned to the fermentor 10, and an extractant/ethanol/water stream 52, which is further processed in the extractant separator 30.

Figure 6:
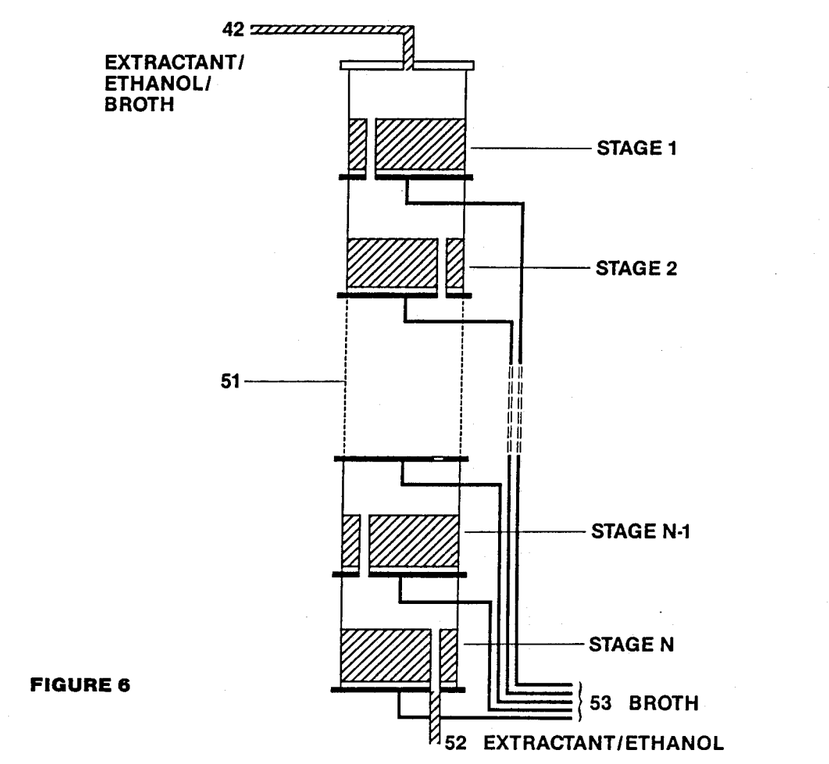
FIG. 6 is a cross sectional view of one embodiment of a broth separator used in the apparatus in FIG. 5.

FIG. 6 shows one embodiment of the broth separator 51 in the form of a gravity settler comprising a plurality of individual settling chambers arranged in series one below the other, into which the extractant/ethanol/broth stream 42 is separated into stream 53 extracted from the bottom of each chamber, consisting largely of fermentation broth, and stream 52 extracted as a overflow from the top of each chamber, consisting largely of extractant and ethanol. The separation efficiency of this device is defined by the size and number (n) of the individual settling chambers, and by the flowrate of stream 53, which is returned to the fermentor.

Figure 7:
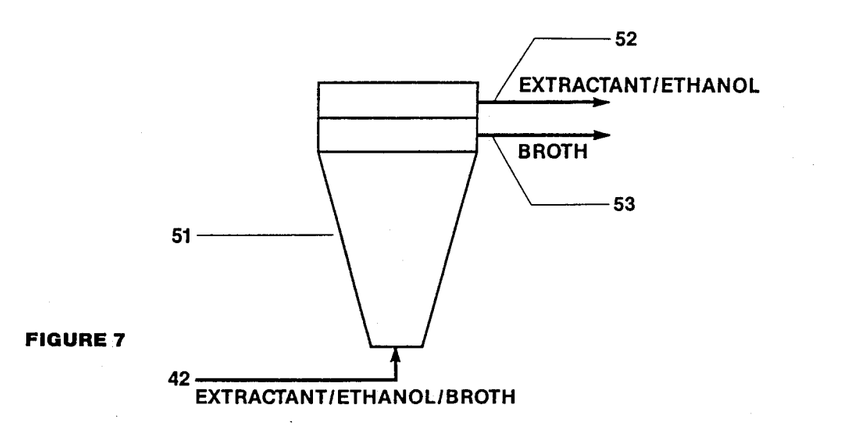
FIG. 7 is a sketch of an alternative broth separator used in the apparatus of FIG. 5.

FIG. 7 shows an alternative embodiment of the broth separator 51 in the form of a centrifuge, in which the extractant/ethanol/broth stream 42 is separated into stream 53, consisting largely of fermentation broth, and stream 52, consisting largely of extractant and ethanol. The separation efficiency of this device is defined by the equipment size, and by the rotation of the centrifuge.

The apparatus thus operates continuously for the production of ethanol while avoiding the problem of end product inhibition.

EXAMPLES

As noted above, a particular advantage of the present invention is that it permits the liquid-liquid extraction to be carried out in situ in a continuous stirred tank fermentor.

To determine the technical and economic advantages of such a process various experiments were carried out as described below. The abbreviations used in the description of these experiments are given in the following nomenclature:

| Nomenclature | |
|---|---|
| Conv. | Glucose conversion = (So—S)/So*100 |
| DENS | Density, g/ml |
| DEtOH | Ethanol distribution coefficient, $[EtOH]_s/[EtOH]_a$ |
| Ds | Extractant dilution rate = Fs/V, $h^{-1}$ |
| Dw | Aqueous dilution rate = Fw/V, $h^{-1}$ |
| EE | Extraction efficiency = PDs/PDtot*100 |
| Fs | Extractant flowrate, L/h |
| Fw | Medium flowrate, L/h |
| Hvap | Latent heat of vaporization at normal boiling point, cal/g |
| LD50 | Lethal dose fifty = the dosage of solvent that will |

| | -continued |
|---|---|
| | Nomenclature |
| | kill 50% of a rat population, in g solvent/kg rat |
| MP | Melting point, deg. C. |
| NBP | Normal boiling point, deg. C. |
| Pw | Effluent aqueous ethanol concentration, g/L |
| Ps | Effluent ethanol concentration in solvent, g/L |
| PDa | Aqueous ethanol productivity = Pw*Dw, g/L-h |
| PDs | Extractant ethanol productivity = Ps*Ds, g/L-h |
| PDtot | Total ethanol productivity = PDa + PDs, g/L-h |
| So | Initial glucose concentration, g/L |
| S | Effluent aqueous glucose concentration, g/L |
| V | Working volume of fermentor = volume of aqueous phase, L |
| X | Effluent aqueous cell concentration, g/l |

The equipment employed as shown in FIG. 4 of the drawings.

Demonstration of Technical Advantages

Below are shown data for two experiments with in situ extractive fermentation of a 159 g/L glucose feed to ethanol in a continuous stirred tank fermentor with a working volume of 1 liter. The microorganism used was the yeast Saccharomyces cerevisiae NCNY 716. The experimental data have been compared to data obtained using an advanced computer model developed by the authors [Kollerup and Daugulis, Biotechnology & Bioengineering, September 1985].

The technical feasibility of extractive fermentation in a CSTF (Continuous Stirred Tank Fermentor) as well as the adequacy of the model are clearly evident from these data. It is particularly important to note the improvement in system performance when operating in the extractive fermentation mode, as measured by % Conversion, and total ethanol productivity (PDtot).

Simulated Fermentation Data For Three Different Operating Conditions.

| PARAMETER | OPERATING CONDITION | | |
|---|---|---|---|
| | (1) | (2) | (3) |
| So, g/L | 150 | 150 | 500 |
| Dw, h-1 | 0.077 | 0.167 | 0.149 |
| S, g/L | 2.6 | 10.0 | 10.0 |
| X, g/L | 10.8 | 10.8 | 45.9 |
| Pw, g/L | 67.3 | 30.3 | 36.7 |
| Conversion, % | 98.3 | 93.3 | 98.0 |
| PDtot, g/L-h | 5.2 | 11.2 | 42.5 |
| Ds, h-1 | — | 1.0 | 5.0 |
| Ps, g/L | — | 6.1 | 7.3 |
| DEtOH, g/g | — | 0.2 | 0.2 |
| EE, % | — | 54.6 | 87.1 |

Approximate mass balances were calculated for the above three operating conditions and costs were projected based on (i) medium pretreatment and waste treatment costs, (ii) ethanol recovery costs, and (iii) fermentor cost. In this analysis, the following assumptions were made:

Medium pretreatment and waste treatment costs are directly proportional to the amount of water in the medium and waste stream, respectively.

Ethanol recovery costs are calculated for the distillation to azeotropic ethanol (95% w/w) from the combination of the streams from lines 43 and 45. [The energy of distillation is taken from R. C. Righelato, "Anaerobic Fermentation: Alcohol Production", Trans Roy. Soc. London B, 290–303 (1980)].

The fermentor cost is assumed to be proportional to $(V)^{0.6}$, where V is the working volume of the fermentor.

Experimental and Predicted Performance Data for Conventional and Extractive Fermentations in a Continuous Stirred Tank Fermentor.

| PARAMETER | EXPERIMENT #1 | EXPERIMENT #2 |
|---|---|---|
| So, g/L | 159 | 159 |
| Dw, h-1 | 0.168 | 0.220 |
| Ds, h-1 | 1.067 | 3.217 |
| DEtOH, g/g | 0.174 | 0.110 |
| pH | 4.0 | 4.0 |
| temperature, deg. C. | 30.0 | 30.0 |
| agitation speed, RPM | 100 | 100 |

| | OPERATION | | | | | | | |
|---|---|---|---|---|---|---|---|---|
| | Conventional | | Extractive | | Conventional | | Extractive | |
| | PRED | EXP | PRED | EXP | PRED | EXP | PRED | EXP |
| S, g/L | 76.8 | 84.1 | 15.6 | 10.3 | 106.7 | 102.3 | 43.5 | 27.8 |
| X, g/L | 5.1 | 4.7 | 9.4 | 9.9 | 3.4 | 2.9 | 7.9 | 10.1 |
| Pw, g/L | 36.6 | 33.4 | 31.5 | 32.3 | 23.6 | 25.2 | 21.0 | 27.8 |
| Conv., % | 51.7 | 47.1 | 90.2 | 93.5 | 32.9 | 35.7 | 72.6 | 82.5 |
| PDtot, g/L-h | 5.8 | 5.6 | 11.2 | 11.3 | 5.2 | 5.5 | 12.1 | 13.3 |
| Ps, g/L | — | — | 5.5 | 5.5 | — | — | 2.3 | 2.6 |
| EE, % | — | — | 52.7 | 52.0 | — | — | 61.8 | 61.5 |

Demonstration of Economic Advantages

In the following, three different operating conditions of a CSTF were considered, namely (1) Conventional CSTF with 15% glucose feed, (2) Extractive CSTF with 15% glucose feed, and (3) Extractive CSTF with 50% glucose feed. These three conditions were simulated with the above mentioned computer model, since the model evidently agreed well with experimental data. The aqueous dilution rate under the three conditions was the dilution rate giving the maximum total ethanol productivity.

RELATIVE COSTS ASSOCIATED WITH DIFFERENT OPERATING CONDITIONS.

| | (1) | (2) | (3) |
|---|---|---|---|
| water in the aqueous feed | 72.1 | 75.1 | 17.5 |
| waste water from beer stripper | 66.9 | 70.9 | 14.2 |
| TOTAL WATER (Waste + Pretreatment) | 139.0 | 145.8 | 31.7 |
| W/P COST relative to (1) | 1.00 | 1.05 | 0.70 |
| STREAMS to Ethanol Distillation Column | | | |
| water | 72.1 | 75.1 | 17.5 |

-continued

| RELATIVE COSTS ASSOCIATED WITH DIFFERENT OPERATING CONDITIONS. | | | |
| --- | --- | --- | --- |
| | (1) | (2) | (3) |
| ethanol | 5.2 | 5.2 | 5.2 |
| TOTAL (distil. column feed) | 77.3 | 80.3 | 22.7 |
| percent ethanol in STREAM | 6.7% | 6.5% | 22.9% |
| energy of distillation/ gross ethanol combustion energy | 0.25 | 0.26 | 0.175 |
| DISTILLATION COST relative to (1) | 1.00 | 1.04 | 0.70 |
| Fermentor volume (L) | 1.00 | 0.464 | 0.122 |
| FERMENTOR COST relative to (1) | 1.00 | 0.63 | 0.28 |

From the above analysis it can be seen that extractive fermentation provides substantial cost savings, particularly when concentrated glucose feeds are fermented. The use of the extractants of the invention makes extractive fermentation in a CSTF feasible.

Although preferred embodiments of the invention have been described above various modifications and alternatives to the above embodiments will be apparent to persons skilled in the art. All such modifications and alternatives form part of this invention provided they do not depart from the scope thereof as defined by the following claims.

We claim:

1. A process for the continuous production of a product selected from ethanol, penicillin, citric acid and polysaccharides by fermentation with a microorganism capable of producing said product and being selected from *Saccharomyces cerevisiae* of *Zymomonas mobilis, Penicillium chrysogenum, Aspergillus niger* and *Pullularia pullulans* respectively, which process comprising culturing said microorganism in an aqueous fermentation medium in a fermentation vessel while continuously introducing an aqueous solution containing a substrate for the microorganism into said fermentation vessel and continuously removing said product from said medium by contacting said medium in situ with a continuiously introduced liquid which is an extractant for said product but which is substantially immiscible with said aqueous medium, and wherein said extractant is fully biocompatible with the selected microorganism and is at least one compound selected from the group consisting of (A) double bond unsaturated aliphatic alcohols having 12 or more carbon atoms; (B) saturated branched chain aliphatic alcohols having 14 or more carbon atoms or mixtures thereof; (C) double bond unsaturated aliphatic acids having 12 or more carbon atoms; (D) aliphatic and aromatic mono-, di- or tri-esters having 12 or more carbon atoms, other than dibutyl phtalate; (E) aliphatic noncyclic ketones and aliphatic aldehydes having 12 or more carbon atoms; and (F) mixtures of extractants from groups (A) to (E) above or mixtures of at least one of the above extractants and at least one other extractant.

2. A process according to claim 1 wherein said extractant is selected from the group consisting of oleyl alcohol, phytol, isophytol, isostearyl alcohol, isocetyl alcohol, octyl dodecanol, oleic acid, linoleic acid, ricinoleic acid, dodecyl acetate, butyl dodecanoate, dibutyl sebacate, di(2-ethylhexyl)sebacate, dibutyl adipate, di(2-ethylhexyl)adipate, di(2-ethylhexyl)phthalate, di(3,5,5-trimethylhexyl)phthalate, glycerol tridecanoate, 2-dodecanone and dodecanal.

3. A process according to claim 1 wherein said fermentation vessel is a continuous stirred tank fermentor.

4. A process according to claim 1 wherein said microorganism is freely suspended in said fermentation medium.

5. A process according to claim 1 wherein, after contacting the fermentation medium with said extractant, said extractant is separated from the medium and subjected to a procedure for separation of the product from the extractant.

6. A process according to claim 5 wherein said procedure comprises distillation of said extractant.

7. A process according to claim 5 wherein said procedure comprises stripping of the product from the extractant by contact with a gas, followed by condensation of the product.

8. A process according to claim 5, wherein, after said procedure, the extractant is recirculated into said fermentation vessel containing said fermentation medium.

9. A process according to claim 5 wherein medium entrained in said extractant separated from the medium is stripped from said extractant prior to said procedure.

10. A process according to claim 9 wherein said medium stripped from said extractant is recirculated to a fermentation vessel containing said fermentation medium.

11. A process according to claim 1 wherein the microorganism is either *Saccharomyces cerevisiae* or *Zymomonas mobilis,* and the product is ethanol.

12. A process for preparing a product selected from ethanol, penicillin, citric acid and polysaccharides by fermentation with a microorganism capable of producing said product and being selected from *Saccharomyces cerevisiae* or *Zymomonas mobilis, Penicillium chrysogenum, Aspergillus niger* and *Pulularia pullulans* respectively, which process comprises:

continuously introducing an aqueous solution containing a substrate for the microorganism into a continuous stirred tank fermentor containing an aqueous fermentation medium and said microorganism in freely suspended form;

continuously withdrawing said aqueous fermentation medium from the fermentor at a rate substantially equal to the rate of introduction of said substrate solution;

continuously introducing a liquid into said fermentation to contact the fermentation medium, said liquid being an extractant for the product selected from the group consisting of (A) double bond unsaturated aliphatic alcohols having 12 or more carbon atoms; (B) saturated branched chain aliphatic alcohols having 14 or more carbon atoms or mixtures thereof; (C) double bond unsaturated aliphatic acids having 12 or more carbon atoms; (D) aliphatic and aromatic mono-, di- or tri-esters having 12 or more carbon atoms, other than dibutyl phthalate; (E) aliphatic noncyclic ketones and aliphatic aldehydes having 12 or more carbon atoms: and (F) mixtures of extractants from groups (A) to (E) above or mixtures of at least one of the above extractants and at least one other extractant;

continuously withdrawing said liquid from the fermentor after said contact with the fermentation medium at a rate substantially equal to the rate of introduction of the liquid into the fermentator; and separating said product from the liquid withdrawn from the fermentor and recirculating the remaining liquid to the fermentor as at least part of the liquid being introduced therein.

* * * * *